US012605755B2

(12) United States Patent　　(10) Patent No.:　　US 12,605,755 B2

Manceau et al.　　(45) Date of Patent:　　Apr. 21, 2026

(54) METHOD FOR MANUFACTURING A CONNECTING ROD FOR ATTACHMENT ELEMENTS SECURED TO THE BODY OF A PATIENT, DEVICE AND CONNECTING ROD FOR CARRYING OUT THE METHOD

(71) Applicant: CLARIANCE, Beaurains (FR)

(72) Inventors: Thierry Manceau, Gieres (FR); Pierric Deransart, Saint Martin d'Uriage (FR); Jean Emmanuel Cardon, Domene (FR)

(73) Assignee: CLARIANCE, Beaurains (FR)

( * ) Notice: Subject to any disclaimer, the term of this patent is extended or adjusted under 35 U.S.C. 154(b) by 359 days.

(21) Appl. No.: 18/017,015

(22) PCT Filed: Jul. 22, 2021

(86) PCT No.: PCT/FR2021/051372

§ 371 (c)(1),
(2) Date: Jan. 19, 2023

(87) PCT Pub. No.: WO2022/018384

PCT Pub. Date: Jan. 27, 2022

(65) Prior Publication Data

US 2023/0347400 A1　　Nov. 2, 2023

Related U.S. Application Data

(60) Provisional application No. 63/056,365, filed on Jul. 24, 2020.

(51) Int. Cl.
*A61B 34/10*　　(2016.01)
*A61B 17/70*　　(2006.01)
(Continued)

(52) U.S. Cl.
CPC ............ *B21D 7/12* (2013.01); *A61B 17/7011* (2013.01); *A61B 17/8863* (2013.01);
(Continued)

(58) Field of Classification Search
CPC ............................ A61B 34/10; A61B 17/7011
See application file for complete search history.

(56) References Cited

U.S. PATENT DOCUMENTS

2009/0249851 A1 * 10/2009 Isaacs ..................... A61B 17/02
　　　　　　　　　　　　　　　　　　　　　72/31.04
2013/0345757 A1 * 12/2013 Stad ................... A61B 17/7011
　　　　　　　　　　　　　　　　　　　　　606/279
(Continued)

FOREIGN PATENT DOCUMENTS

WO　　　2019/217208　　11/2019

OTHER PUBLICATIONS

International Search Report for PCT/FR2021/051372, mailed Nov. 24, 2021, 8 pages.
(Continued)

*Primary Examiner* — Mark A Connolly
(74) *Attorney, Agent, or Firm* — NIXON & VANDERHYE

(57)　　　　　　ABSTRACT

Disclosed is a method for manufacturing a connecting rod between attachment elements secured to the spine of a patient, the method including: —planning the manufacturing of a first virtual rod based on the patient's anatomical data, —positioning and securing the attachment elements on the patient's body, —intraoperatively acquiring the position of the attachment elements for the purpose of creating a second virtual rod, —analyzing the first and second virtual rods for the purpose of creating a third virtual rod, —intraoperatively manufacturing a real rod from the third virtual rod by a (Continued)

PC1

100　　TV1　　TV2　　TV3 bending device. Also disclosed are the device and the connecting rod allowing the method to be carried out.

20 Claims, 7 Drawing Sheets

(51) Int. Cl.
A61B 17/88 (2006.01)
B21D 7/12 (2006.01)
A61B 17/00 (2006.01)
A61B 17/56 (2006.01)

(52) U.S. Cl.
CPC .... A61B 34/10 (2016.02); *A61B 2017/00526* (2013.01); *A61B 2017/568* (2013.01); *A61B 2034/104* (2016.02)

(56) References Cited

U.S. PATENT DOCUMENTS

| | | | | |
|---|---|---|---|---|
| 2019/0336179 A1* | 11/2019 | Pak | ........................ | A61B 34/10 |
| 2020/0015857 A1 | 1/2020 | Rout et al. | | |
| 2020/0345420 A1* | 11/2020 | Hobeika | ................ | A61B 34/10 |
| 2022/0117664 A1* | 4/2022 | Junio | ................ | A61B 17/7011 |
| 2024/0079146 A1* | 3/2024 | Schmidt | ................ | G06T 7/0012 |

OTHER PUBLICATIONS

Written Opinion of the ISA for PCT/FR2021/051372, mailed Nov. 24, 2021, 7 pages.

* cited by examiner

PC2

PC2 ⟶          TV1

PC1

200

100

METHOD FOR MANUFACTURING A CONNECTING ROD FOR ATTACHMENT ELEMENTS SECURED TO THE BODY OF A PATIENT, DEVICE AND CONNECTING ROD FOR CARRYING OUT THE METHOD

BACKGROUND OF THE INVENTION

Field of the Invention

The invention relates to the field of surgery and in particular to the manufacture of a rod for connecting attachment elements secured to the body of a patient.

Description of the Related Art

The manufacture of a rod for connecting attachment elements secured to the body of a patient such as a rod for connecting pedicle screws and/or vertebral hooks can be carried out in different ways.

A preoperative method so-called "planning" exists, which consists in taking x-rays of the patient, identifying the angular corrections of the vertebrae, including the sacrum, virtually correcting the images by working on the x-rays, modelling a virtual connecting rod taking into account the correction and, by modeling the positioning of the attachment elements, manufacturing a connecting rod which is provided to the surgeon, intended to be to be fixed to the patient.

In practice, the surgeon must often correct manually in the operating room during surgery the preformation of the rod due to the various intraoperative hazards, particularly with regard to the actual position of the attachment elements and their solidity.

Document WO2019217208 describes a system for intraoperatively manufacturing a vertebral rod to be placed on the spine of a patient, which comprises:

a profiled substitution spinal rod, a scanning assembly designed to scan the profiled substitution spinal rod and to produce a first model based on the scan, a control unit adapted to receive the first model and perform at least one analysis on the first model, and a bending assembly adapted to receive the first model from the control unit and to manufacture the spinal rod based on the first model.

Such a system requires the presence of a substitution rod and ensures the acquisition of the position of the attachment elements by means of the acquisition and the shape of the substitute rod before the manufacture of the final rod which can be placed without correction by the surgeon.

Such a system does take intraoperative hazards into account, but in certain situations can cause part of the correction objective to be lost provided it only takes into account data from the patient.

In addition, such a system must guarantee aseptic conditions during the acquisition and manufacturing operations of the rod.

SUMMARY OF THE INVENTION

The applicant conducted research aimed at improving the manufacturing method of such a rod by improving the conditions of sterility during the bending of the actual rod.

This research led to the design of a new method for manufacturing a connecting rod and a device for carrying it out.

According to the invention, the method for manufacturing a rod for connecting attachment elements secured to the spine of a patient is remarkable in that it includes the following steps:

planning the manufacturing of a first virtual rod based on the patient's anatomical data, positioning and securing the attachment elements on the patient's body, intraoperatively acquiring the position of the attachment elements for the purpose of creating a second virtual rod, analyzing the first and second virtual rods for the purpose of creating a third virtual rod, intraoperative manufacturing an actual rod from the third virtual rod, by the use of a bending device.

This method is particularly advantageous in that it combines the advantages of existing methods and avoids, by selecting the phases, their disadvantages. Indeed, neither the planning nor the intraoperatively acquiring of the actual positions of the attachment elements lead directly to the manufacture of a rod. These two steps are only implemented for the purpose of creating virtual rods which, taken together, contribute to the production of the actual rod.

This method constitutes a compromise between preoperative planning and the position of the screws observed intraoperatively.

Indeed, the manufacture of the final rod takes into account:

Surgical gestures performed intraoperatively (osteotomies/releases, etc.) at the same time as securing the attachment means, which the planning could not take into account;

The holding strength of the screws or of the fastening means in the bone evaluated intraoperatively, which the planning could not take into account;

The resistance of the rod;

Bending angles made possible;

Rod length that can be manufactured;

The rigidity of the desired assembly (selection of the constituent material of the rod (TA6V, CoCr depending on the state of finish, CFR-PEEK or other suitable materials) possibly in connection with a completed element calculation software;

The actual intraoperative position and the type of attachment elements put in place, with their orientation for receiving the rod (tulip oriented upwards, downwards, laterally, etc.) and their cone of mobility (polyaxial, monoaxial, uniplanar screw); Which are parameters that could not be taken into account together in the methods of the prior art. Moreover, while the simple intraoperatively acquiring could lose sight of the correction ultimately desired, taking into account the first virtual rod makes it possible to return to the primary objectives while taking into account the intraoperative constraints and the constraints of the bending device.

The anatomical data necessary to the planning can be obtained by any suitable medical imaging means: X-ray, IRM, Scanner, Ultrasonography . . . .

The function of acquiring the position of the attachment elements is to obtain data allowing the virtual creation and deformation of the second virtual rod ensuring the connection between said attachment elements by being installed on the latter. These data will be used by the bending device of the invention.

The attachment elements can be associated with poles or temporary rods allowing them to get as close as possible to their final position. Nevertheless, the acquisition of the positions of these attachment elements has the purpose of creating the second virtual rod.

The second virtual rod is capable to be virtually deformed to not only ensure the connection but also to correct the positions by creating by its shape a stress on one or more connected attachment elements. The desired correction was defined by the creation of the first virtual rod.

In addition, the method is remarkable in that it may comprise a correcting operation for correcting the third virtual rod for the purpose of creating a fourth virtual rod to be manufactured.

According to another particularly advantageous feature of the invention, the analysis phase consists in superimposing the second virtual rod on the first virtual rod.

Combined or not with this type of analysis, an algorithmic analysis is also planned.

According to one embodiment, the first virtual rod is represented in the correction position.

According to another particularly advantageous feature, the method is remarkable in that the acquisition is carried out with an instrument and at least one optical, infrared or depth camera.

According to another particularly advantageous feature, the method is remarkable in that the acquisition is carried out by a scanner or a mobile camera. These means identify the receiving space formed by the attachment elements for the rod, make a point pass through the center of the receiving spaces, and connect the points to make a spline therewith, representative of the second virtual intraoperative rod. The camera can be onboarded on a tablet or on extended reality glasses for example.

According to another particularly advantageous feature, the method is remarkable in that it includes a positioning operation for positioning markers near or on the attachment elements for acquisition purposes. The acquisition is carried out by placing, prior to the acquisition, a visual or infrared marker near or on the attachment elements.

The shape and dimensions of this marker in combination with at least two shots ensure the three-dimensional virtual reproduction of the attachment elements.

This is a simple and inexpensive method for optimizing the acquisition of this type of data.

Once this second virtual rod has been defined, a manufacturing/bending program is implemented. This program takes into account the first virtual rod and obtains a resulting rod to finally produce an actual rod by a manual or automated bender.

Another object of the invention relates to a new device for bending the connecting element so as to better comply with the constraints related to sterilization since the bending is carried out intraoperatively.

The bending device for bending a rod for connecting attachment elements secured to the body of a patient, while the manufacture takes into account the positioning of the attachment elements, is equipped with driving and bending means for driving and bending the rod.

According to the invention, it comprises a sterilizable part equipped with at least driving and bending means for driving and bending the rod and a non-sterilized part equipped with the motorization of said means or with the battery powering the motorization of said means.

To do this, the sterilizable part is connected to the motor shafts projecting from the non-sterilized part. Sealing gaskets arranged between the sterilized part and the non-sterilized part implement sealing. According to another embodiment, the motors are also sterilizable and only the batteries constitute the non-sterilized part.

This bending is done in three dimensions. To do so, the bending device is equipped with a drive mandrel ensuring rotation of the rod around its longitudinal axis and translation of the latter along this longitudinal axis so as to make bending in three dimensions possible. The bending device is further equipped with a bending mandrel making it possible to bend the rod around an axis orthogonal to the longitudinal axis.

The manufacturing program may result from data acquisition carried out on the patient.

The method then comprises a sterilizing operation for sterilizing the sterilizable part before driving and bending the rod to be bent.

Another solution making it possible to comply with the constraints related to sterilization consists in a packaging the rod being adapted and resistant to the stresses resulting from the bending of the rod.

According to another feature of the invention, the connecting rod is packaged/encapsulated in a flexible container adapted to at least a sterilization method and resistant to the stresses resulting from the bending of the rod.

This new packaging consists in packaging/encapsulating the sterile rod before bending so as to comply with the constraints related to sterilization despite the fact that the connecting rod must undergo a bending operation.

This feature makes it possible to optimize the sterilization conditions offered besides by the device.

Thus, according to another feature, the manufacturing method includes a bending operation using a bending device for bending the packaged/encapsulated rod.

According to another feature, aiming at the encapsulation or the packaging not to interfere with the bending, at least one end is pre-formed with an indexing geometric profile, for, on the one hand, allowing good grip of the encapsulation/packaging on the sterile rod to be deformed and, on the other hand, making it possible to control the deformation.

According to another feature, said container is peelable.

To the extent that the rod obtained does not conform to what was expected or that it requires an a posteriori correction, it is possible to repeat the method according to a corrected resulting virtual rod. The correction of the virtual rod can be linked in particular to a new acquisition of the attachment elements or linked to a correction operation carried out in a software interface by the surgeon. During the repetition of the method, a new rod can be bent, or the rod obtained before correction can be placed again in the bending device.

The fundamental concepts of the invention having just been explained above in their most elementary form, other details and features will emerge more clearly on reading the description which follows and with regard to the appended drawings, describing, by way of non-limiting example, an embodiment of a method, a device and a rod in accordance with the invention.

5

Figure 3:
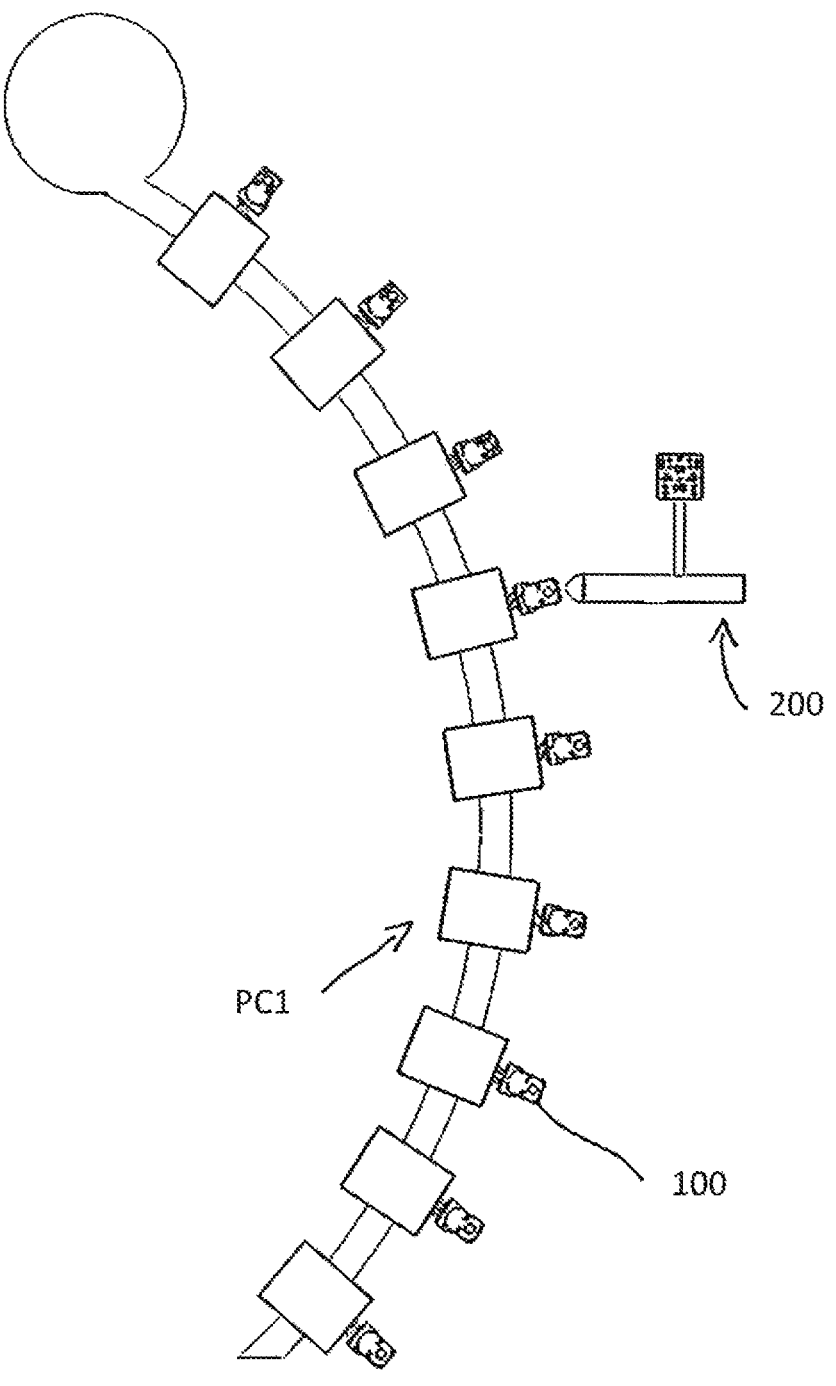
Figure 4:
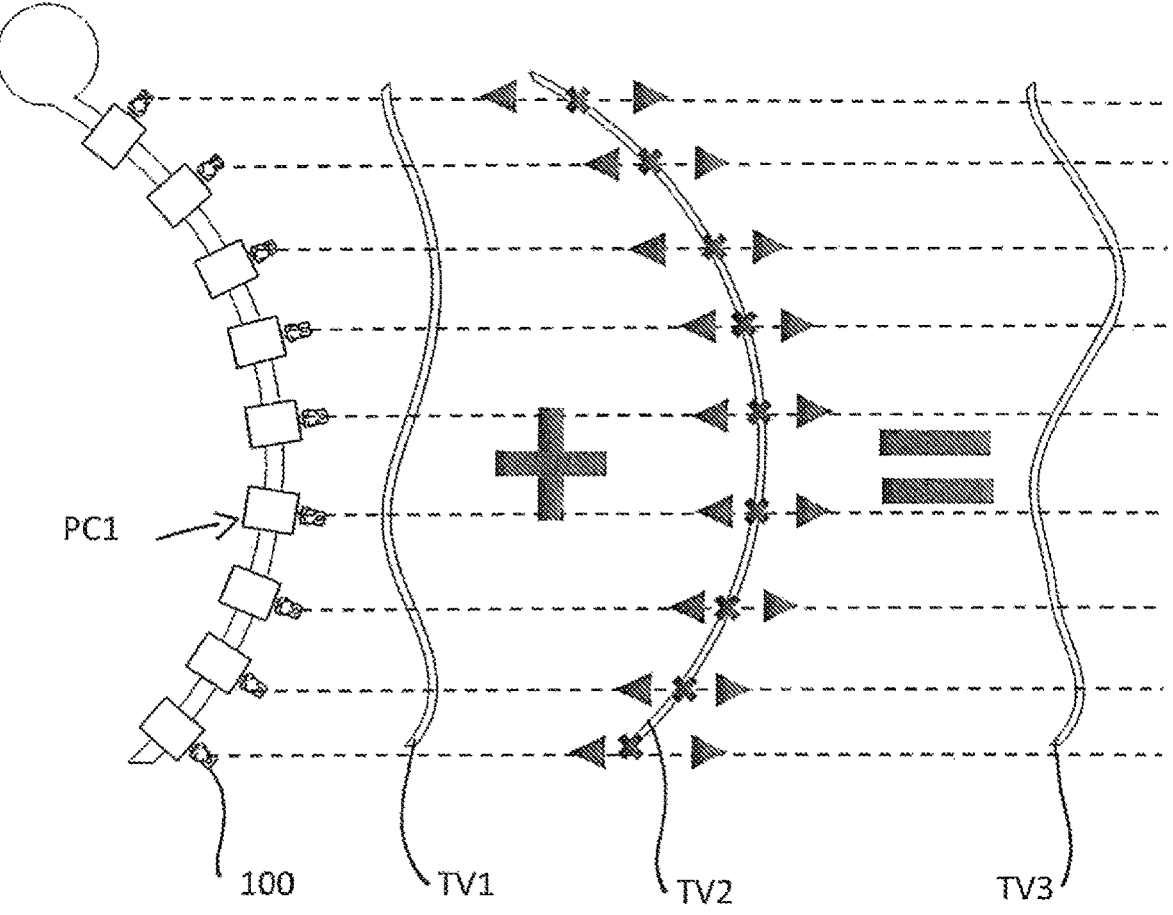
Figure 5:
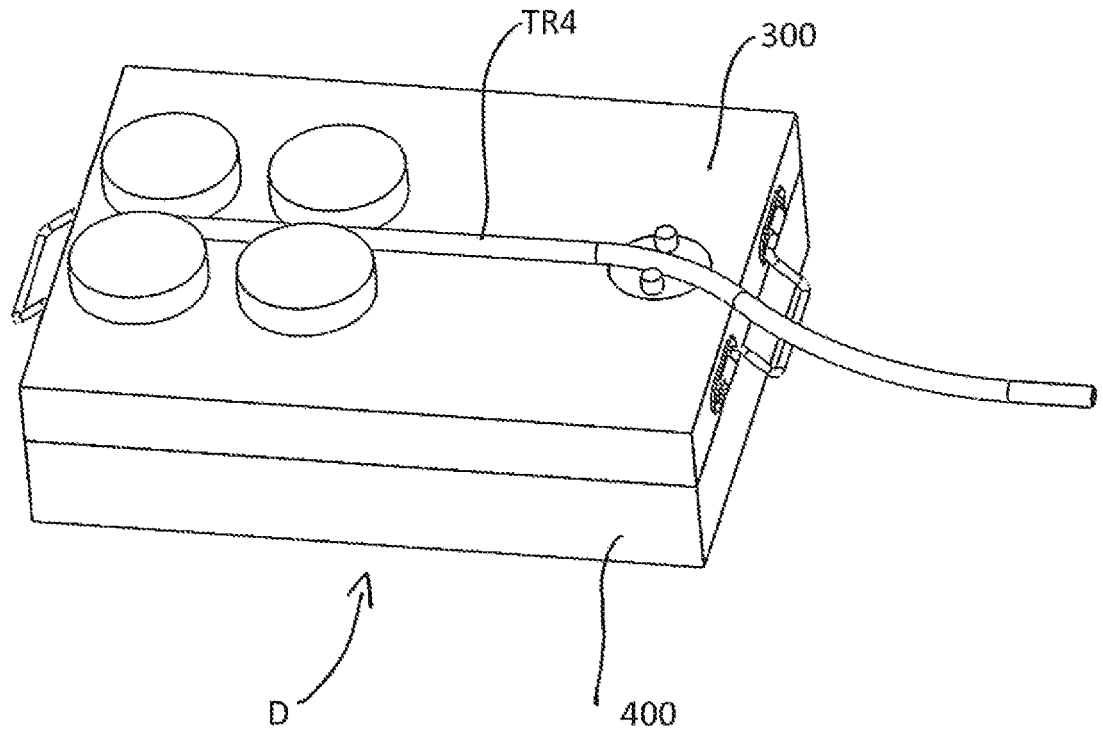
Figure 6:
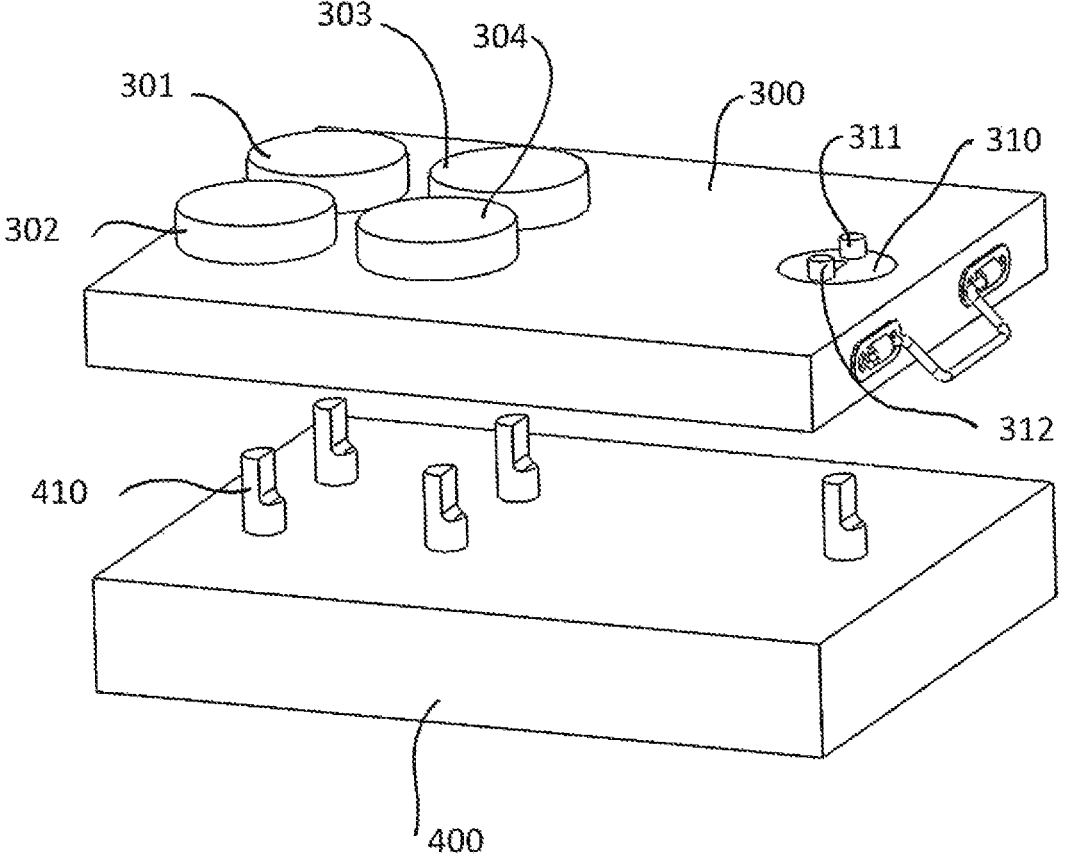
Figure 7:
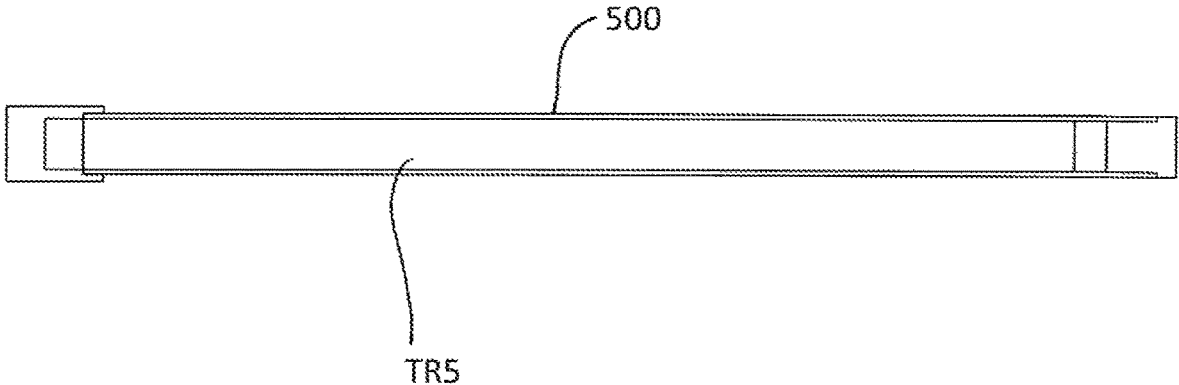

FIG. 3 is a schematic drawing of the portion of the spine to be corrected with the attachment elements attached to it;

FIG. 4 is a schematic drawing showing in mutual correspondence the sagittal view of a portion of the spine with the attachment elements attached to it, the first virtual rod, the second virtual rod and the resulting rod whose manufacture will be ordered;

FIG. 5 is a perspective view of one embodiment of a bender according to the invention;

FIG. 6 is an exploded perspective view of said bender;

FIG. 7 is a drawing of one embodiment of a packaged sterile rod.

DESCRIPTION OF A PREFERRED EMBODIMENT

The drawing in FIG. 3 schematically shows a portion of a patient's spine PC1, which spine requiring correction by means of attachment elements connected by a connecting rod.

In accordance with the invention, in order to manufacture this connecting rod, the practitioner will carry out a planning operation for the manufacture of a first virtual rod.

Figure 1:
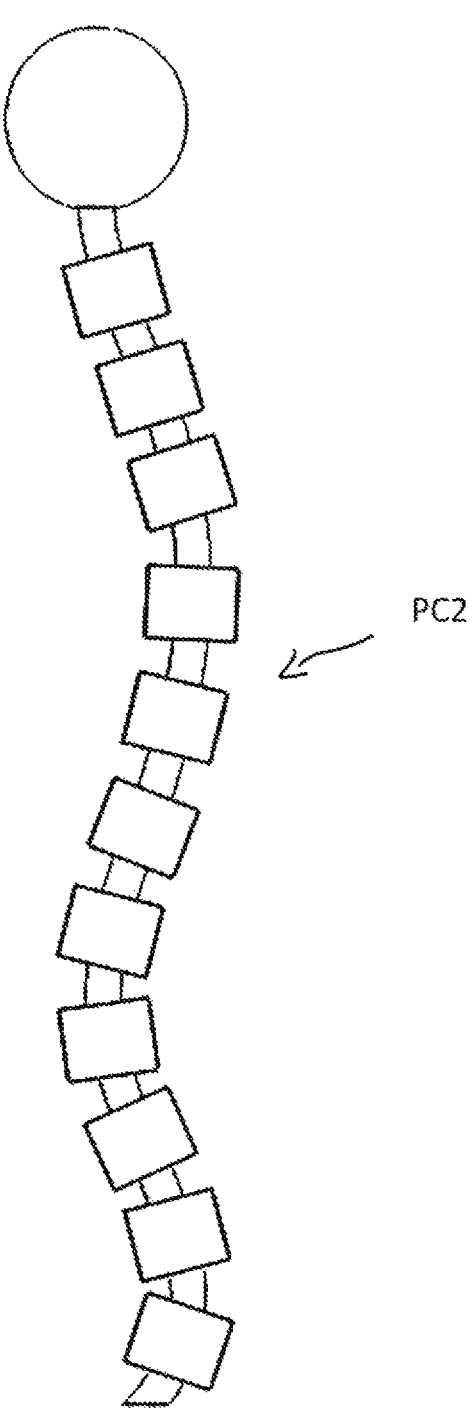
FIG. 1 is a schematic drawing of a sagittal view of a portion of the spine with the desired correction corresponding to the equivalent of an x-ray image revised so as to be corrected.

To do this, on the basis of anatomical data (such as one or more x-rays) shown in a simplified way by FIG. 3, the practitioner will imagine a corrected portion of spine PC2 as shown in FIG. 1.

Figure 2:
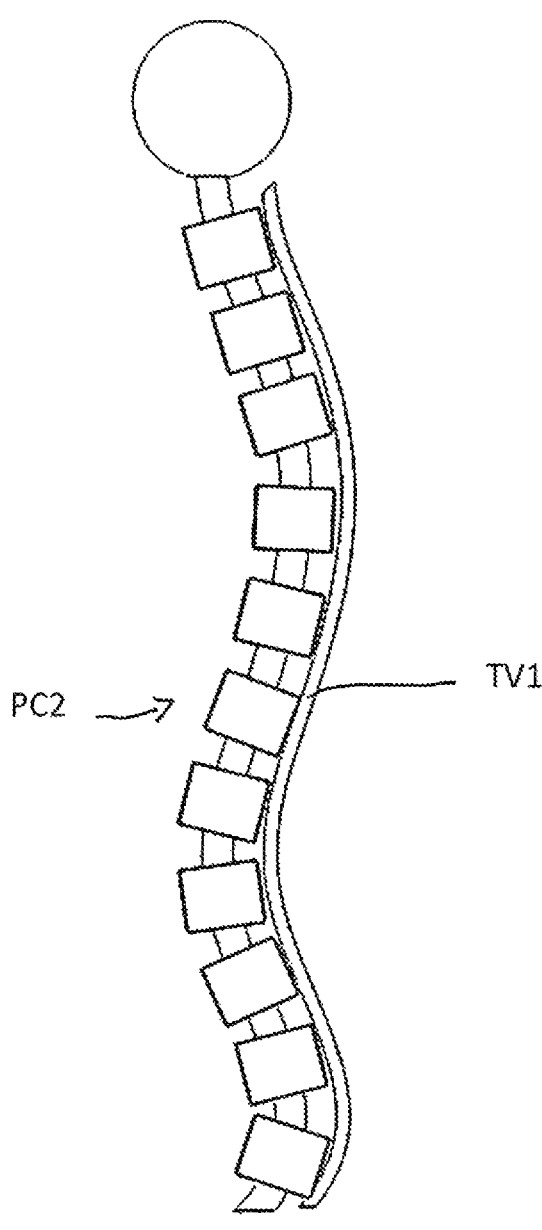
FIG. 2 is a schematic drawing of the portion of the spine with the first modelized virtual rod.

In order to implement this correction, a first virtual rod TV1 is defined as shown in FIG. 2.

Attachment elements 100 are then attached to the portion of the patient's spine PC1 to be corrected, as shown in FIG. 3.

Still as shown in this figure, the position of the attachment element 100 is acquired by means of an instrument 200. The instrument makes it possible to locate the receiving spaces provided by the attachment elements for receiving the rod and to acquire, by means of software, a point at the center of the receiving spaces. Then, the software means connects the points to make a spline representative of the second virtual rod which takes into account the intraoperative conditions. Indeed, this acquisition makes it possible to take account of the actual attachment points of the rod on the portion of spine PC1 and leads to defining a second virtual rod TV2.

As shown in FIG. 4, the analysis of the first virtual rod TV1 and the second virtual rod TV2 leads to the creation of a third virtual rod TV3.

The intraoperative manufacturing of an actual TR4 rod from this third virtual TV3 rod (itself corrected or not by means of a software solution) by a bending device can then be performed.

An embodiment of a bending device D is shown by FIGS. 5 and 6. As shown, this bending device D making it possible to manufacture the actual rod TR4 (shown during manufacture in FIG. 5) is remarkable in that it comprises at least one sterilizable part 300 equipped with driving and bending means for driving and bending the rod TR4 and a non-sterilized part 400 equipped with the motorization of said means and/or the battery to power the motorization of said means.

The sterilizable part 300 covers here and is connected to the motor shafts 410 projecting from the non-sterilized part 400.

This sterilizable part 300 comprises two pairs of rollers 301, 302 and 303, 304 for driving the rod TR4 in translation along its longitudinal axis to pass it through a bending tool 310 consisting of a disc on which are positioned, diametrically opposite one with respect to the other, two cylindrical lugs 311 and 312. Driven by the rollers, the rod TR4 is positioned between the two lugs 311 and 312 whose rotation ensures the deformation. According to an embodiment not shown, the device comprises a single pair of rollers.

According to a feature not shown, device D is also equipped with a mandrel ensuring the rotation of the rod TR4 around its longitudinal axis so as to make the bending possible in three dimensions.

Another solution envisaged for keeping a bent rod sterile consists, as shown in FIG. 7, in packing it while it's straight so as to comply with the constraints related to sterilization despite the fact that the connecting rod must undergo a bending operation. Thus, the rod TR5 to be bent is packaged in a flexible container 500 suitable for at least one method of sterilization and resistant to the stresses resulting from bending of the rod.

In order to facilitate gripping by the mandrel (not shown) but also to avoid displacement of the packaging/encapsulation 500 during bending, at least one end of the TR5 rod is pre-formed with an indexing profile.

According to a preferred embodiment, this indexing is implemented by a hexagonal profile or by a hexalobular profile such as that known under the trademark "Torx".

It is to be understood that the method, the device and the rod which have just been described and represented above, were described for the purpose of disclosure rather than limitation. Of course, various arrangements, modifications and improvements may be made to the above example, without departing from the scope of the invention.

The invention claimed is:

1. A method for manufacturing a rod for connecting attachment elements secured to the spine of a patient, the method comprising:

planning manufacturing of a first virtual rod based on anatomical data of the patient;

positioning and securing the attachment elements on the body of the patient;

intraoperatively acquiring the position of the positioned and secured attachment elements to create a second virtual rod;

analyzing the first and the second virtual rods to create a third virtual rod based on the analyzed first and second virtual rods; and intraoperatively manufacturing an actual rod from the third virtual rod, by a bending device.

2. The method according to claim 1, further comprising correcting the third virtual rod to create a fourth virtual rod to be manufactured.

3. The method according to claim 2, wherein the acquiring the position of the positioned and secured attachment elements is carried out with an instrument and at least one optical or infrared or depth camera.

4. A bending device for bending a rod for connecting attachment elements secured to the body of a patient implementing the method according to claim 2, further comprising a sterilizable part equipped with at least driving and bending means for driving and bending the rod and a non-sterilized part equipped with the motorization of said means or with the battery powering the motorization of said means.

5. The method according to claim 1, wherein the analyzing comprises superimposing the second virtual rod on the first virtual rod.

6. The method according to claim 5, wherein the acquiring the position of the positioned and secured attachment elements is carried out with an instrument and at least one optical or infrared or depth camera.

7. A bending device for bending a rod for connecting attachment elements secured to the body of a patient implementing the method according to claim 5, further comprising a sterilizable part equipped with at least driving and bending means for driving and bending the rod and a non-sterilized part equipped with the motorization of said means or with the battery powering the motorization of said means.

8. The method according to claim 1, wherein the acquiring the position of the positioned and secured attachment elements is carried out with an instrument and at least one optical or infrared or depth camera.

9. A bending device for bending a rod for connecting attachment elements secured to the body of a patient implementing the method according to claim 8, further comprising a sterilizable part equipped with at least driving and bending means for driving and bending the rod and a non-sterilized part equipped with the motorization of said means or with the battery powering the motorization of said means.

10. The method according to claim 1, wherein the acquiring the position of the positioned and secured attachment elements is carried out by a scanner or a mobile camera.

11. The method according to claim 10, further comprising positioning markers near or on the attachment elements to acquire the position of the positioned and secured attachment elements.

12. A bending device for bending a rod for connecting attachment elements secured to the body of a patient implementing the method according to claim 11, further comprising a sterilizable part equipped with at least driving and bending means for driving and bending the rod and a non-sterilized part equipped with the motorization of said means or with the battery powering the motorization of said means.

13. A bending device for bending a rod for connecting attachment elements secured to the body of a patient implementing the method according to claim 10, further comprising a sterilizable part equipped with at least driving and bending means for driving and bending the rod and a non-sterilized part equipped with the motorization of said means or with the battery powering the motorization of said means.

14. A bending device for bending a rod for connecting attachment elements secured to the body of a patient implementing the method according to claim 1, further comprising a sterilizable part equipped with at least driving and bending means for driving and bending the rod and a non-sterilized part equipped with the motorization of said means or with the battery powering the motorization of said means.

15. The device according to claim 14, wherein the sterilizable part is connected to the motor shafts projecting from the non-sterilized part.

16. The device according to claim 15, wherein sealing gaskets arranged between the sterilized part and the non-sterilized part implement sealing.

17. The device according to claim 14, wherein the device is equipped with a drive mandrel ensuring rotation of the rod around the rod's longitudinal axis and translation of this rod along this longitudinal axis so as to make bending in three dimensions possible.

18. A rod for connecting attachment elements, enabling performing method according to claim 1, wherein the rod is packaged/encapsulated in a flexible container adapted to at least a sterilization method and resistant to the stresses resulting from the bending of the rod.

19. The connecting rod according to claim 18, wherein at least one end of the rod is pre-formed with an indexing geometric profile.

20. The connecting rod according to claim 18, wherein said container is peelable.

* * * * *